(12) United States Patent
Odendall et al.

(10) Patent No.: US 8,286,462 B2
(45) Date of Patent: Oct. 16, 2012

(54) METHOD FOR DIAGNOSING THE RELIABILITY PERFORMANCE OF A JUMP PROBE

(75) Inventors: Bodo Odendall, Lenting (DE); Stefan Rosenberger, Ingolstadt (DE); Torsten Knebel, Ismaning (DE); Martin Schneider, Pietenfeld (DE)

(73) Assignee: Audi AG, Ingolstadt (DE)

( * ) Notice: Subject to any disclaimer, the term of this patent is extended or adjusted under 35 U.S.C. 154(b) by 581 days.

(21) Appl. No.: 12/467,756

(22) Filed: May 18, 2009

(65) Prior Publication Data

US 2009/0282891 A1 Nov. 19, 2009

(30) Foreign Application Priority Data

May 16, 2008 (DE) .......................... 10 2008 023 893

(51) Int. Cl.
*G01N 21/00* (2006.01)
(52) U.S. Cl. ........................................ 73/1.06
(58) Field of Classification Search .................. None
See application file for complete search history.

(56) References Cited

U.S. PATENT DOCUMENTS

| | | | | |
|---|---|---|---|---|
| 5,394,744 A * | 3/1995 | James et al. | ............... | 73/114.02 |
| 6,439,038 B1 * | 8/2002 | Rosel et al. | ............... | 73/114.73 |
| 6,668,545 B2 * | 12/2003 | Brown | ............................ | 60/284 |
| 7,311,093 B2 * | 12/2007 | Hayashi et al. | ............... | 123/688 |

FOREIGN PATENT DOCUMENTS

| | | | |
|---|---|---|---|
| DE | 197 22 334 A1 | 12/1998 | |
| DE | 10 2004 005 520 A1 | 9/2004 | |
| DE | 60 2004 006 664 T2 | 4/2007 | |

* cited by examiner

*Primary Examiner* — Robert R Raevis
(74) *Attorney, Agent, or Firm* — Novak Druce + Quigg, LLP

(57) ABSTRACT

In a change from a lean to a rich exhaust gas mixture, a characteristic behavior appears in a short time interval in the vicinity of the lambda jump of an upstream catalytic converter lambda probe in the signal characteristic which is measured by a downstream catalytic converter lambda probe. From the signals in small intervals, around the instant of changing, the reliability performance of the downstream lambda probe can be deduced without the actual probe jump in curves of the voltage characteristics having to be considered.

17 Claims, 2 Drawing Sheets

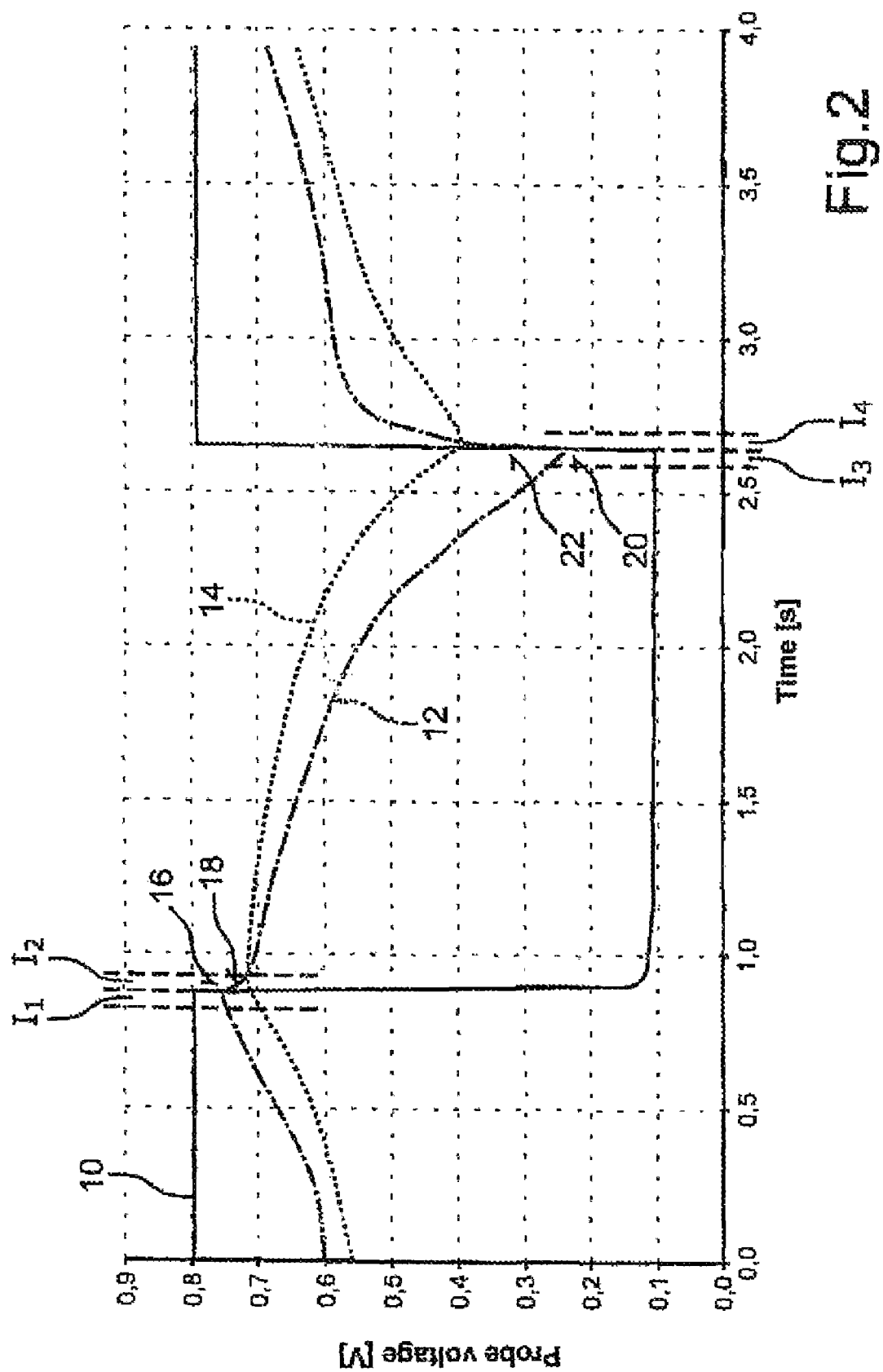

METHOD FOR DIAGNOSING THE RELIABILITY PERFORMANCE OF A JUMP PROBE

The invention relates to a method for diagnosing the reliability performance of a lambda probe which is made as a so-called jump probe. The quantity "lambda" designates the ratio of air to fuel in an exhaust gas. A jump probe delivers a voltage signal which changes suddenly when a certain value of lambda is exceeded. Typically the jump is at $\lambda=1$, when in the exhaust gas there is the exact amount of air to burn all the fuel in the exhaust gas.

BACKGROUND OF THE INVENTION

The jump probe addressed here, also referred to as the first jump probe below, is designed to be located in the exhaust line in the outflow direction of an exhaust gas emerging from an internal combustion engine downstream from at least one section of a catalytic converter with an oxygen storage capacity.

The catalytic converter has the capacity to store oxygen so that short-term deviations from the ideal air-fuel ratio $\lambda=1$ can be buffered. A control system results in that the extreme cases in which no oxygen at all is stored in the catalytic converter or the oxygen storage reservoir is full do not occur. In the control process the voltage measurement signals of the jump probe to be analyzed are used. Typically, the value of $\lambda$ oscillates during control around the value $\lambda=1$. At this point, the jump probe can deliver an adulterated signal due to ageing. By adulterating the signal, faulty operation can occur during control. It is therefore necessary to make available a method for diagnosing the reliability performance of the indicated jump probe in the installed state in the exhaust gas line.

DE 10 2005 016 075 A1 describes a method for diagnosis of the reliability performance of a lambda probe. In this connection, exhaust gas is supplied to the exhaust gas line, intentionally a sudden change is used in the air-fuel ratio from a rich exhaust gas mixture (an exhaust gas mixture with more fuel than can be burned by the air present) to a leaner exhaust gas mixture (an exhaust gas mixture with more air than necessary to burn the fuel which is present) or vice versa. The change in the air-fuel ratio leads to a jump in the voltage which is acting as the measurement signal. DE 10 2005 106 075 A1 describes that a time interval is measured between the detection of such a jump in the signal of a lambda probe located upstream from the catalytic converter and the detection of a jump in the signal of a lambda probe downstream from the catalytic converter. It is assumed here that this time interval is additively composed of the contribution which is dictated by the oxygen storage capacity of the catalytic converter and the contribution which is dictated by the probe properties. The individual contributions can be deduced according to a certain procedure. The contribution dictated by the probe properties is examined according to a threshold value criterion for whether the probe can be classified as performing reliably or not.

DE 198 28 929 A1 describes a method for checking the dynamic behavior of a measurement transducer in the exhaust gas line of an internal combustion engine in which likewise a change in the air-fuel mixture is used: The signal of the measurement transducer during a regeneration phase is monitored and faulty dynamic behavior is diagnosed when the predetermined signal characteristic is absent.

The disadvantage of the method used in the prior art for diagnosing the reliability performance of a downstream catalytic converter lambda probe is that the oxygen storage capacity of the catalytic converter must be taken into account in the evaluation of the signals. But this is mostly itself an unknown, in particular, the oxygen storage capacity of the catalytic converter can have decreased by its poisoning; this causes effects which cannot be distinguished at all or can hardly be distinguished from the effects caused by probe ageing.

Thus the object of the invention is to make available a method for diagnosing the reliability performance of a lambda probe in the initially described arrangement which can be easily carried out and which is still especially reliable.

SUMMARY OF THE INVENTION

As is conventional in the prior art, in a changing sequence lean exhaust gas and rich exhaust gas are supplied to the exhaust gas line in order to cause in alternation the absorption of oxygen by the catalytic converter (especially up to the capacity limit) and the (especially complete) re-release of the absorbed oxygen by the catalytic converter. According to the invention, for diagnosis purposes at least one signal is used which has been received from the first lambda probe when changing from lean to rich exhaust gas or vice versa.

Preferably only those signals which have been picked up by the first lambda probe during a change are used.

The received signal thus has nothing more to do with a jump in the measurement signals of the lambda probe, since this is only the consequence of the change and therefore occurs after it, not during it. If, for example, lean exhaust gas is supplied first, oxygen accumulates in the oxygen storage reservoir of the catalytic converter. When changing to rich exhaust gas, a jump at the lambda probe does not take place directly since the rich exhaust gas removes from the oxygen storage reservoir the oxygen stored in it. Only when the amount of stored oxygen is reduced and the signal on the lambda probe changes distinctly can a jump be determined. The invention is based on the finding that in a change between the lean and rich exhaust gas or vice versa the indicated buffer effect does not occur in perfect form, but that the change can be recognized on the measurement signal of the lambda probe. Especially for a change in the measurement signals of a fully reliably performing lambda probe does a characteristic peak occur which corresponds to an inflection point in the curve. When the lambda probe ages, the peak is attenuated and finally becomes no longer detectable.

To have found this characteristic in the probe signals beyond the voltage jumps is the achievement of the inventor of this invention. The method according to the invention uses the knowledge to analyze the signal or signals in a change according to a predetermined criterion in order to diagnose whether the lambda probe is performing reliably or not.

The characteristic signal in the measurement signal of the lambda probe occurs when the new exhaust gas, that is, that supplied after the change, arrives for the first time at the lambda probe (jump probe). The exchange of oxygen between the exhaust gas and catalytic converter cannot prevent the change from being recognizable exactly at this instant in the probe signal.

Signals of a central control unit which causes the changing supply of lean and rich exhaust gas can be evaluated, but preferably to ascertain when the change takes place, another lambda probe is used which is referred to as the second lambda probe in the following. It is to be located in the exhaust gas line (in the flow direction of the exhaust gas) upstream from the first lambda probe, typically a least one catalytic converter segment, preferably the entire catalytic converter, being located between the two lambda probes. The second lambda probe is conventionally located entirely upstream from the catalytic converter, while the first lambda probe which is to be subjected to diagnosis here is located in the catalytic converter or downstream from it.

The second lambda probe can now determine the instant of a change (from lean to rich or vice versa), for example, when a voltage value which indicates the jump is exceeded. Depending on this instant, a time interval is now defined. One or more signals picked up in this time interval by the first lambda probe are used for diagnosis, preferably solely signals from this time interval.

The time interval can now begin directly with the instant of changing. When refined, the time interval, however, begins around the estimated or determined passage time after the instant of change, and the passage time is that time which the exhaust gas requires for passage through the exhaust gas line from the second jump probe to the first jump probe.

The time interval can be comparatively short relative to the time scale of the change. Preferably, it has a length of at most 50 ms, especially preferably, less than 20 ms. One typical value for the time interval is 10 ms, its beginning around 5 to 10 ms after the instant of change in the signal of the second lambda probe in order to take into account the gas transit time. It should be noted that conversely a time scale of 0.5 to 2.5 s must be assigned to these times intervals, with which scale the supply of lean or rich exhaust gas takes place. The time interval from which the signals for diagnosis are used during a change is therefore at most a tenth as large, preferably at most a twentieth or even a fiftieth as large as the time interval between a change from lean to rich or vice versa.

The specific signal to be analyzed can be recognized from its time behavior so that preferably the time derivative of the voltage signal of the lambda probe at least one instant from the time interval is used to define the numerical value of the derivative which is used for diagnosis. The numerical value of the derivative can be the maximum amount of the time derivative in the time interval, but also the average amount of this time derivative. The numerical value of the derivative is typically compared according to a predetermined criterion to a threshold value by which it is established whether the first probe is considered to be performing reliably or not. Instead of establishing the numerical value of the derivative directly with such a threshold value, it can also be set in a ratio to another numerical value of the derivative as the reference numerical value of the derivative and the magnitude of the ratio which has been obtained in this way can then be compared to a threshold value according to a predetermined criterion by which it is ascertained whether the first probe is considered to be performing reliably or not. The other numerical value of the derivative is determined using at least one signal of the first lambda probe in another time interval which is prior to the time interval determined depending on the instant of the change (and preferably for its part is defined depending on the instant of the change). The further time interval can be directly prior to the first time interval or, for safety in considering the transit time of the exhaust gas through the exhaust gas line from the second lambda probe to the first lambda probe in the definition of the first time interval, can be prior to the instant of change.

The other numerical value of the derivative which is used for the magnitude of the ratio can be the minimum amount of the time derivative in the further time interval especially when the above defined numerical value of the derivative is the maximum amount of the time derivative in the time interval. If, for the first numerical value of the derivative, the average amount of the time derivative in the time interval is used, preferably the average amount of the time derivative, and specifically in the further time interval, is likewise used for the further numerical value of the derivative.

DETAILED DESCRIPTION OF THE PREFERRED EMBODIMENTS OF THE INVENTION

Figure 1:
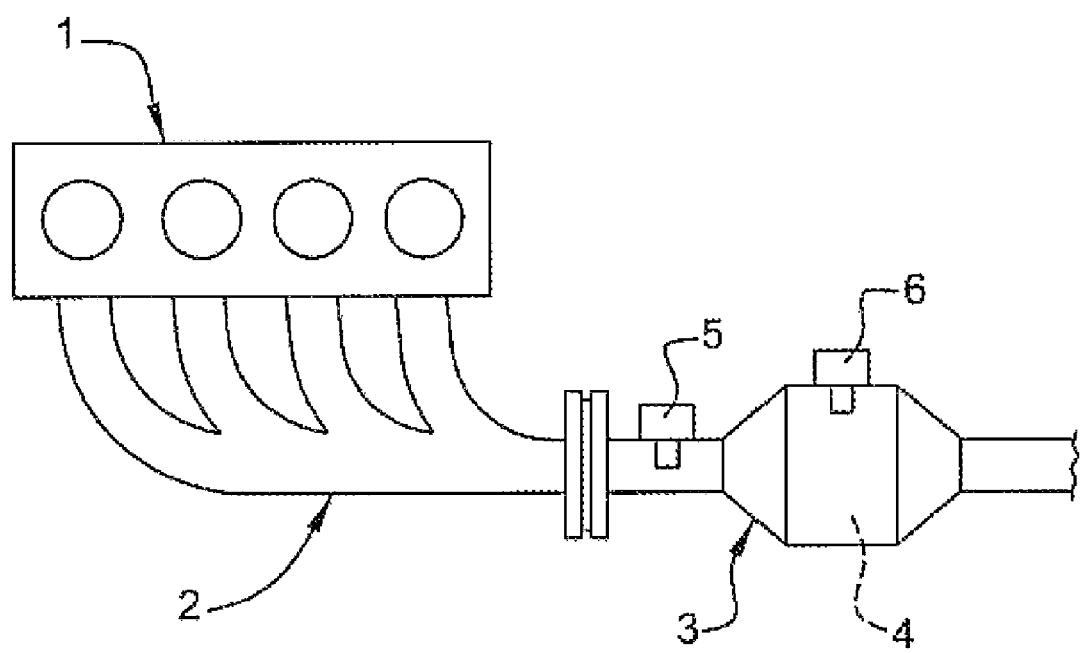
FIG. 1 shows an arrangement in which use of the method according to the invention is beneficial and FIG. 2 schematically shows the curve behavior of an upstream catalytic converter probe and a downstream catalytic converter probe.

FIG. 1 shows a schematic of an internal combustion engine 1 with an exhaust gas line 2. The exhaust gas line 2 comprises an exhaust gas catalytic converter 3 which is made, for example, as a three-way catalytic converter, as a NOx storage catalytic converter or as an active particle filter and contains an integrated oxygen storage reservoir 4. The exhaust gas line 2 furthermore comprises a lambda probe 5 which is located upstream from the exhaust gas catalytic converter 3 and which is used as a guide probe, and a lambda probe 6 which is assigned to the exhaust gas catalytic converter 3 and which is used as a control probe.

The lambda probe 6 in this embodiment is located downstream from the exhaust gas catalytic converter 3. This lambda probe, however, could also be located equally well directly in the exhaust gas catalytic converter 3, i.e., after a partial volume of the oxygen storage reservoir 4.

It is assumed below that the exhaust gas of the internal combustion engine can be set to a given air-fuel ratio $\lambda$ at least with a defined accuracy.

Here a lean exhaust gas mixture and a rich exhaust gas mixture are delivered in a changing sequence. The lambda probe 5 then measures the voltage signals which are reproduced in the curve 10. It can be clearly recognized that the voltage jumps back and forth between a value of 0.8 V and a value of 0.1 V. The jumps are relatively steep so that unique instants can be assigned to them, for example, using a threshold value criterion (0.45 V is exceeded or not reached, or the like).

In measurement of the curve 10 by the probe 5, the probe 6 measures the signals according to curve 12 when it is performing fully reliably, for example, when it is new. The probe 6 measures signals according to curve 14 when it is no longer performing adequately reliably, for example, due to ageing.

Curves 12 and 14 differ in the characteristic in a time window from 1.0 to 2.5 s which is given according to the example after the (arbitrarily set here) time zero point. Typically, using this characteristic the degree of ageing of the probe can be deduced. The characteristic is interpreted here in particular as the probe voltage jump even if curves 12 and 14 in this respect do not exhibit the steepness of curve 10.

Here it is not the characteristic in the probe voltage between 0.7 and 0.2 V which is at the focus of interest. Rather a time interval in the region around the change from lean to rich exhaust gas and vice versa which can be detected using curve 10 is at the center of interest. The time interval $I_1$ before the change and the time interval $I_2$ after the change can be established. The boundary between the intervals can be shifted by the estimated transit time relative to the jump in curve 10 since the exhaust gas must traverse the path from the lambda probe 5 to the lambda probe 6. This transit time is, however, extremely small relative to the time dimensions which are shown in FIG. 2, and therefore cannot be detected in it. In the region of the time intervals $I_1$ and $I_2$ the curve characteristic in curve 12 which is measured by a reliably performing probe changes drastically: there is a characteristic inflection point 16 in curve 12, after the inflection point 16 the curve 12 falling especially steeply in the region 18 of curve 12.

For a probe which is not performing completely reliably the effect of filtering becomes apparent. Filtering in an aged probe takes place in particular such that a pronounced inflection point can no longer be recognized in the manner of the inflection point 15 in curve 14. A steep drop after this inflection point does not occur either.

To detect the reliability performance of a probe it is therefore enough to examine the interval $I_2$ alone or to compare the curve characteristic in the interval $I_2$ to the one in the interval $I_1$. The steep drop in the region 18 of curve 12 is reflected in a quantitatively high value of the time derivative, averaged over the interval $I_2$. The absence of this steep drop in curve 14 is reflected in a comparatively quantitatively small value of the averaged time derivative in the interval $I_2$. It is therefore sufficient to compare these average values to one another, for example, to establish a ratio value. If a threshold value is not reached by this ratio value, the probe can be diagnosed as no longer performing reliably enough. Since curve 12 is flatter in the region in front of the inflection point 16 than curve 14 in the interval $I_1$, differences in the curve behavior are expressed even more strongly in this ratio value than in the absolute values for the average time derivative in the interval $I_2$ which certainly could be used even without the values from $I_1$ for diagnosis.

Analogous considerations can be made for intervals $I_3$ and $I_4$ for the reverse change in a voltage jump up in curve 10. Thus, using the values in the interval $I_4$, optionally with consideration of the values in the interval $I_3$, it can be deduced whether the probe is performing fully reliably or not. In curve 12 here a pronounced inflection point 20 and a steep characteristic of the curve in region 22 also appear, while for curve 14 the behavior is greatly attenuated, specifically by the effect of filtering based on ageing of the probe.

The invention claimed is:

1. A method for diagnosing the reliability performance of a first lambda probe which is located in the exhaust gas line in the outflow direction of an exhaust gas emerging from an internal combustion engine downstream from at least one section of a catalytic converter with an oxygen storage capacity, in which in a changing sequence lean exhaust gas and rich exhaust gas are supplied to the exhaust gas line in order to cause in alternation the absorption of oxygen by the catalytic converter and the re-release of the absorbed oxygen by the catalytic converter, wherein for diagnosis purposes at least one signal is used which has been received from the first lambda probe in the change from one of lean to rich and rich to lean exhaust gas, wherein using a second lambda probe located in the exhaust gas line upstream from the first lambda probe an instant of change is determined and that depending on this instant a time interval is defined and the signals picked up in the time interval by the first lambda probe are used for diagnosis, and wherein the time interval begins around the estimated and averaged transit time after the instant of change, which time the exhaust gas requires to transit the exhaust gas line from the second jump probe to the first jump probe.

2. The method according to claim 1, wherein the time interval has a length in the range of 50 ms to 20 ms.

3. The method according to claim 1 wherein for diagnosis purposes the numerical value of the derivative is used which includes the time derivative of the voltage signal of the first lambda probe at least one instant during the time interval.

4. The method according to claim 3 wherein the numerical value of the derivative is the maximum amount of the time derivative in the time interval.

5. The method according to claim 3 wherein the numerical value of the derivative is the average amount of the time derivative in the time interval.

6. The method according to claim 3 wherein the numerical value of the derivative is compared to a threshold value according to a predetermined criterion by which it is ascertained whether the first probe is considered to be performing reliably or not.

7. The method according to claim 3 wherein from the numerical value of the derivative with a further numerical value of the derivative the magnitude of the ratio is determined which is compared to a threshold value according to a predetermined criterion by which it is established whether the first probe is considered to be performing reliably or not, the further numerical value of the derivative using at least one signal of the first lambda probe being determined in a further time interval which extends from the time interval which has been determined as a function of the instant of change.

8. The method according to claim 7 wherein the further numerical value of the derivative is the minimum amount of the time derivative in the further time interval.

9. The method according to claim 7 wherein the further numerical value of the derivative is the average amount of the time derivative in the further time interval.

10. A method for diagnosing the reliability performance of a first lambda probe which is located in the exhaust gas line in the outflow direction of an exhaust gas emerging from an internal combustion engine downstream from at least one section of a catalytic converter with an oxygen storage capacity, in which in a changing sequence lean exhaust gas and rich exhaust gas are supplied to the exhaust gas line in order to cause in alternation the absorption of oxygen by the catalytic converter and the re-release of the absorbed oxygen by the catalytic converter, wherein for diagnosis purposes at least one signal is used which has been received from the first lambda probe in the change from one of lean to rich and rich to lean exhaust gas, wherein using a second lambda probe located in the exhaust gas line upstream from the first lambda probe an instant of change is determined and that depending on this instant a time interval is defined and the signals picked up in the time interval by the first lambda probe are used for diagnosis, and wherein the time interval has a length in the range of 50 ms to 20 ms.

11. The method according to claim 10 wherein for diagnosis purposes the numerical value of the derivative is used which includes the time derivative of the voltage signal of the first lambda probe at least one instant during the time interval.

12. The method according to claim 11 wherein the numerical value of the derivative is the maximum amount of the time derivative in the time interval.

13. The method according to claim 11 wherein the numerical value of the derivative is the average amount of the time derivative in the time interval.

14. The method according to claim 11 wherein the numerical value of the derivative is compared to a threshold value according to a predetermined criterion by which it is ascertained whether the first probe is considered to be performing reliably or not.

15. The method according to claim 11 wherein from the numerical value of the derivative with a further numerical value of the derivative the magnitude of the ratio is determined which is compared to a threshold value according to a predetermined criterion by which it is established whether the first probe is considered to be performing reliably or not, the further numerical value of the derivative using at least one signal of the first lambda probe being determined in a further time interval which extends from the time interval which has been determined as a function of the instant of change.

16. The method according to claim 15 wherein the further numerical value of the derivative is the minimum amount of the time derivative in the further time interval.

17. The method according to claim 15 wherein the further numerical value of the derivative is the average amount of the time derivative in the further time interval.

* * * * *